(12) United States Patent
Noar

(10) Patent No.: US 7,160,254 B2
(45) Date of Patent: Jan. 9, 2007

(54) INTELLIGENT SELF-INTERPRETING ELECTROVISCEROGRAM SYSTEM AND METHOD

(76) Inventor: Mark Noar, 11 Alterwood La., Owings Mills, MD (US) 21117

( * ) Notice: Subject to any disclaimer, the term of this patent is extended or adjusted under 35 U.S.C. 154(b) by 0 days.

(21) Appl. No.: 11/067,926

(22) Filed: Mar. 1, 2005

(65) Prior Publication Data

US 2005/0215917 A1  Sep. 29, 2005

Related U.S. Application Data

(60) Provisional application No. 60/550,333, filed on Mar. 8, 2004.

(51) Int. Cl.
*A61B 5/08* (2006.01)
*A61B 5/05* (2006.01)

(52) U.S. Cl. .................. 600/538; 600/529; 600/547

(58) Field of Classification Search .............. 600/546, 600/547, 529, 506, 531–538, 484, 483, 481
See application file for complete search history.

(56) References Cited

U.S. PATENT DOCUMENTS

| | | | |
|---|---|---|---|
| 4,846,190 A * | 7/1989 | John | 600/544 |
| 5,144,554 A * | 9/1992 | Zhang et al. | 600/372 |
| 5,318,039 A * | 6/1994 | Kadefors et al. | 600/546 |
| 5,623,925 A * | 4/1997 | Swenson et al. | 600/301 |
| 5,701,894 A * | 12/1997 | Cherry et al. | 600/546 |
| 5,704,368 A | 1/1998 | Asano | |
| 5,857,980 A * | 1/1999 | Wilson | 600/546 |
| 6,171,244 B1 * | 1/2001 | Finger et al. | 600/437 |
| 6,249,697 B1 * | 6/2001 | Asano | 600/546 |
| 6,351,665 B1 | 2/2002 | Koch | |

* cited by examiner

*Primary Examiner*—Charles A Marmor, II
*Assistant Examiner*—Navin Natnithithadha
(74) *Attorney, Agent, or Firm*—Manelli Denison & Selter; Edward J. Stemberger

(57) ABSTRACT

A method detects and interprets myoelectrical activity from an intra-abdominal organ. Electrodes obtain first signals over time relating to myoelectrical activity of organ. A respiration sensor obtains second signals relating to respiration of the patient. An initial parameter range of the first and second signals is established. A processor determines minutes when artifact occurs in both the first and second signals based on the initial parameter range. It is then determined whether there are artifact free minutes of the first and second signals. A condition of the patient is changed after determining that there are sufficient artifact free minutes. The first and second signals are recorded in memory simultaneously for a period of time after changing the condition of the patient. A processor determines whether artifact occurs in the recorded first and second signals. Artifact free minutes of the recorded first and second signals are selected for analysis. Via the processor, the selected minutes are analyzed to automatically determine a condition of the organ.

28 Claims, 3 Drawing Sheets

INTELLIGENT SELF-INTERPRETING ELECTROVISCEROGRAM SYSTEM AND METHOD

This application is based on U.S. Provisional Application No. 60/550,333, filed on Mar. 8, 2004, claims the benefit thereof for priority purposes, and is incorporated herein by reference for all purposes.

FIELD OF THE INVENTION

The invention relates to a system and method for detecting myoelectrical activity of intrabdominal (gastrointestinal) organs, identifying artifact, selecting ideal signal for interpretation, and providing computer analysis and interpretation of the signal.

BACKGROUND OF THE INVENTION

Nausea, bloating, post-prandial fullness, early satiety, increased eructus, bowel irregularity, abdominal pain, and vomiting are symptoms that may be characteristic of a number of different diseases, which affect the stomach and upper or lower gastrointestinal tract. The symptoms may be mild, or may develop into chronic, severe, or even debilitating conditions, which adversely affect the physical and/or mental well being of an individual. The gastroenterologist, internist, or family physician that is evaluating the patient with these symptoms has many difference diseases to consider. The patients may become difficult to manage, especially when standard tests such as barium studies, ultrasound, CAT scan, MRI, and endoscopy are normal, and trials of empiric therapy fail.

Electrogastrograms (EGG) have been employed in the past to diagnose stomach disorders. These devices have been able to collect myoelectrical impulses, and accurately identify spurious signals, which have allowed manual interpretation of signals to assist in the diagnosis of gastrointestinal motility disorders. Current devices have been successful in filtering out spurious signals such as electrocardiographic electrical activity. However, some artifactual signals, such as respiratory signals, occur in frequency ranges of interest. Typically the interpretation of these signals requires manual interpretation and considerable expertise to insure accuracy and uniformity of diagnosis and accuracy of potential treatment. Even once artifact has been excluded, signal interpretation if often variable and based upon the expertise or lack thereof of the end user. Other factors such as the proper functioning of the device and acquisition of the myoelectrical signal may lead to erroneous signal recording and inaccurate subsequent interpretation and diagnosis. Even when signal is accurately acquired, and artifact is eliminated or recognized, experiential factors lead to variability in interpretation and diagnosis.

Recent research conducted with the standard electrogastrogram (EGG), has resulted in the ability to distinguish unique patterns to better diagnose various specific gastric motility disorders, including: 1) gastroesophageal reflux disease, 2) gastric outlet obstruction, and 3) pure gastric rhythm disturbances. In addition, it has been possible to further document resolution or improvement of these conditions following appropriate corrective treatment using the same device platform.

However, the current device platform requires manual post-procedural review and analysis of the signal to determine that the signal was recorded accurately to allow for subsequent manual selection of signal components for interpretation, and to arrive at a diagnostic conclusion, which must then be manually recorded.

Accordingly, there is a need to provide a novel method and system to gather and evaluate myoelectrical signals from intrabdominal and other intra-cavitary, motility based organs, such as the stomach, that will aid in the diagnosis of disorders and identify when said disorders may have been corrected, which is based upon the acquisition of the nascent signals and identification of spurious signals, but also provide for: 1) real-time analysis to allow recognition and correction of faulty signals or processes intra-procedurally, 2) intelligent auto-selection of signal components to be interpreted, 3) auto-interpretation of signals, 4) auto-diagnosis of results, and 5) instant automatic results reporting. Since the system and method are not limited to the stomach, the term "electroviscerogram" (EVG) is used herein.

SUMMARY OF THE INVENTION

An object of the invention is to fulfill the need referred to above. In accordance with the principles of the present invention, this objective is obtained by a method of detecting and interpreting myoelectrical activity from an intra-abdominal organ. Electrodes are used to obtain first signals over time relating to myoelectrical activity of the intra-abdominal organ of a patient. A respiration sensor obtains, simultaneously with the first signals, second signals relating to respiration of the patient. An initial parameter range of the first and second signals is established. A processor determines minutes when artifact occurs in both the first and second signals based on the initial parameter range of the first and second signals. It is then determined whether there are artifact free minutes of the first and second signals. A condition of the patient is changed after determining that there are sufficient artifact free minutes. This could include introducing a water load in the stomach of the patient. The first and second signals are recorded in memory simultaneously for a period of time after changing the condition of the patient. A processor determines whether artifact occurs in the recorded first and second signals based on a comparison with the initial parameter range. Artifact free minutes of the recorded first and second signals are selected for analysis. Via the processor, the selected minutes are analyzed to automatically determine a condition of the organ.

In accordance with another aspect of the invention, a system for detecting and interpreting myoelectrical activity from an intra-abdominal organ is provided. The system includes electrodes constructed and arranged to obtain first analog signals over time relating to myoelectrical activity of the intra-abdominal organ of a patient. A respiration sensor is constructed and arranged to obtain, simultaneously with the first signals, second analog signals relating to respiration of the patient. Filtering structure is constructed and arranged to filter the first and second analog signals. An analog to digital converter is constructed and arranged to convert the filtered first and second analog signals to respective first and second digital signals. A processing device is constructed and arranged to receive the first and second digital signals. The processing device configured for executing instructions for 1) determining whether artifact occurs in the first and second digital signals based on an analysis of the first and second digital signals, and 2) analyzing artifact free minutes of the first and second signals thereby determining a condition of the organ. A storage device is associated with the processing device and is constructed and arranged to store data received from the processing device.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF THE EXEMPLARY EMBODIMENT

U.S. Pat. No. 6,351,665, hereby incorporated by reference into this specification for all purposes, discloses an EGG system that includes of a set of functional subsystems. The first subsystem consists of EGG electrodes, an isolation cable and amplifier/filters that amplifies the low level EGG signal and filters it with a passband of approximately 1–15 cpm. The second subsystem consists of a respiration sensor and amplifier. The third subsystem consists of a strip chart recorder that receives both the EGG and respiration amplified signals for recording on a strip chart. The fourth subsystem consists of an analog to digital converter that receives both the EGG and respiration amplified signals, digitizes these signals and sends them to a computer that is part of the subsystem.

The EGG system of the U.S. Pat. No. 6,351,665 consists primarily of off-the-shelf components. Electrodes are connected to an ISO-Z (Dataq) preamplifier that also provides patient isolation. The preamplifier is a small box (approximately 1.2" high by 3.5" wide by 4.3" deep) connected by a long cable (approximately 6') to a BMA-931 (Dataq) general purpose amplifier that has been modified to provide 0.016 Hz high pass and 0.25 Hz low pass cutoff frequencies. The amplified and filtered signal is then connected to a 12 bit A/D converter PCMCIA card (Measurement Computing) that is inserted into a standard laptop computer, to which is connected a printer. The respiratory sensor connects to a general purpose amplifier (PM-1000, Dataq). The general purpose amplifiers are arranged in a cage housing that is approximately 8" high by 11" wide by 12" deep. Power is supplied to the housing (a standard DC supply), where it is distributed to the general purpose amplifiers; the modified BMA-931 supplies power to the ISO-Z preamplifier. The strip chart recorder is optionally connected to the amplifier cage housing. The system is large, requiring a large cart to hold all the components. It is difficult to setup and maintain due to the varied cables and components of which it is comprised. The bulk of the system increases the anxiety of some patients, making recording of EGG more difficult.

The invention relates generally to methods, apparatus, self-correcting processes, auto-interpretive diagnostics, and results reporting of myoelectric signals from contractile, hollow internal body organs for the purpose of diagnosis of various disorders. The general term for the system of the invention is the intelligent, self-interpreting electroviscerogram (EVG), which measures and self-interprets myoelectrical activity from various organs within a body cavity. Specifically, the invention relates to the use of an electrogastrographic system that acquires, auto-corrects, analyzes, self-interprets, and reports results and diagnoses of recorded signals associated with functional, neurological, or neuromuscular disorders of the gastrointestinal, urinary, or other motility based organs.

Figure 1:
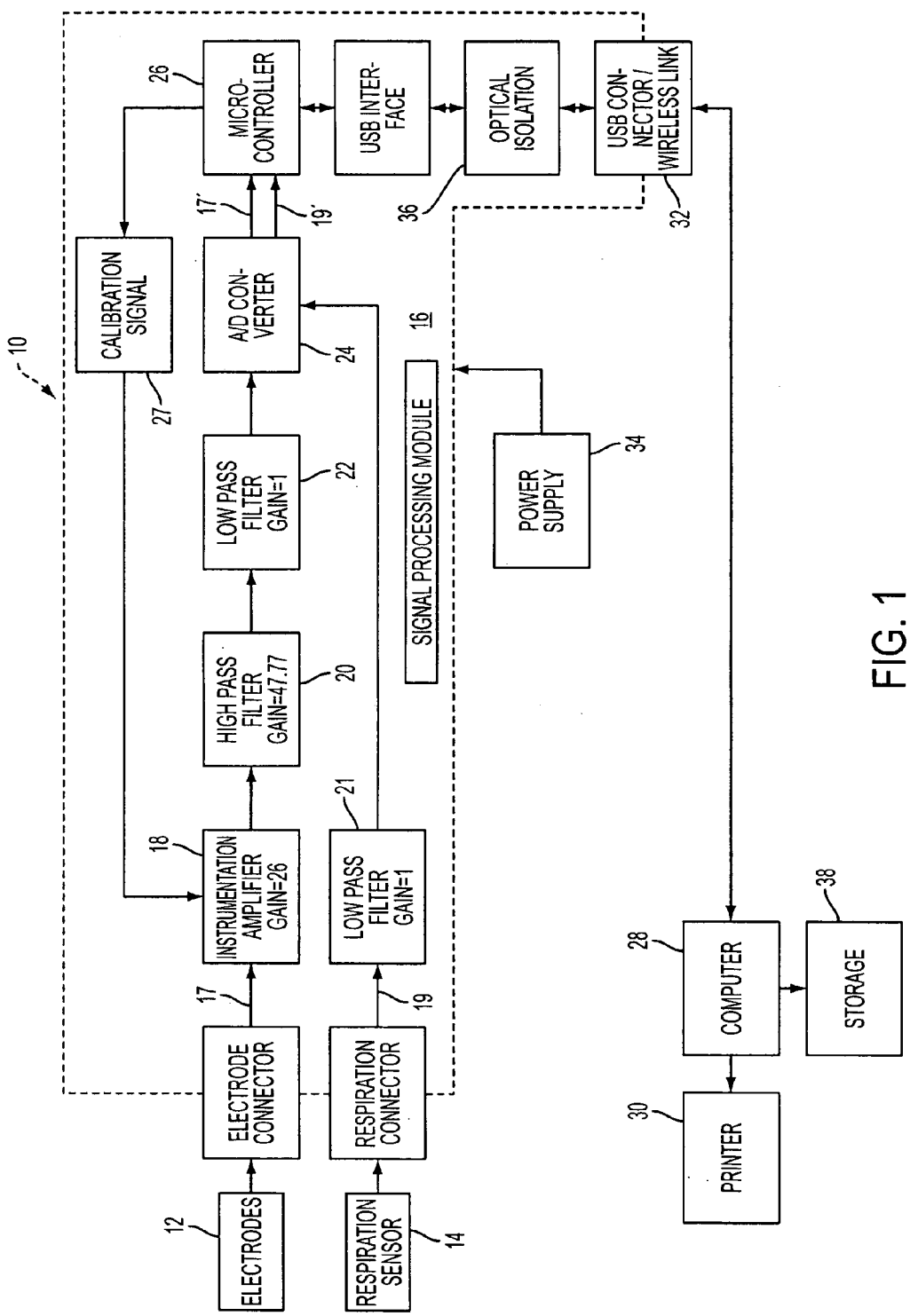
FIG. 1 is a block diagram of an electroviscerogram system provided in accordance with the principles of the present invention.

An embodiment of the EVG System of the invention is a system that results in substantial size and cost savings as compared to the conventional EGG system. A block diagram of an embodiment of the system 10 is shown in FIG. 1. Electrodes 12 (preferably two or three) and a respiratory sensor 14 connect to a single Signal Processing Module 16 (SPM). The SPM 16 is approximately 1" high by 2.5" wide by 4.5" long. A standard instrumentation amplifier 18 provides the first gain stage for the electrode(s) signal 17. A high pass filter 20 provides additional gain and is followed by a low pass filter 22. The respiration signal 19 is filtered by low pass filter 21 and is then passed on to a 16-bit A/D converter 24. The electrode signal 17 is also passed to the on board 16-bit A/D converter 24. The digitized electrode signal 17' and digitized respiration signal 19' are each passed to a microcontroller 26, which coordinates data transfer to a host computer 28 and printer 30 via a standard Universal Serial Bus (USB) connection, or a wireless signal transmitter 32. The A/D converter 24 can be part of the microcontroller 26. The host computer 28 can be considered a processing device.

Power is supplied to the SPM 16 via an internal 9V battery 34 in the preferred embodiment, but power may also be supplied from an external DC supply or via the USB port directly (the latter two require additional patient electrical isolation circuitry, whereas the battery achieves patient electrical isolation directly).

Considerable effort and cost can be applied to the configuration of analog (hardware) filters that provide for suitable attenuation of unwanted frequencies in the acquired EVG signal 17. It has been determined that a more practical approach to the configuration of the analog filters is such that they pass frequencies beyond the ideal passband, then digitally filter these signals after analog-to-digital conversion with a more narrow passband of suitable attenuation. Such digital filters can be made much more accurate than their analog counterparts and are not subject to the same effects of analog component tolerances that lead to less than ideal performance from device to device and over time. Analog components can be manually sorted such that only ideal components are used, but there is considerable cost involved that will drive up the end price to the physician and these components are still subject to the ravages of environmental stresses and time that impairs their accuracy. The preferred embodiment employs a passband comprised of a first or second order high pass analog filter 20 with cutoff frequency in the range 0.001 to 0.016 Hz and a first or second order low pass analog filter 22 with cutoff frequency in the range 0.25 to 0.5 Hz. The configuration of such analog filters is known in the art.

A digital filter is employed in software in the micro controller 26 of the SPM 16 with a high pass cutoff in the range 0.008 to 0.016 Hz and a low pass cutoff in the range 0.25 to 0.3 Hz, generally both of second order, but higher order digital filters can be implemented. An optional second digital filter may be implemented in the software (computer readable medium) of host computer 28 for high pass and/or low pass functions to achieve the desired 0.016 to 0.25 Hz bandpass filtering of EVG signals 17' prior to software analysis. This approach also provides greater flexibility in the system for changing specific frequency ranges in the digital filter to focus on specific aspects of the EVG or any general electroviscerogram waveform; such changes can be controlled by software running on the host computer to allow quick reconfiguration of the system as needed during a particular patient exam.

Gain in the preferred embodiment of the SPM 16 is fixed and set according to the greatest peak to peak EVG signal normally expected. The 16 bit A/D converter 24 provides sufficient resolution to adequately process lower level signals, such as may be recorded from a person with substantial amount of fat tissue interposed between the electrodes on the skin surface and the stomach. Of course, gain may be made controllable either via an analog control or via digital control at additional cost.

Use of the USB connector or wireless transmitter 32 for data communication with the host computer 28 removes the need for cumbersome cables and complicated interfaces that each present distinct possibilities for intermittent or total failure that can degrade system performance. The USB specification allows for cables up to 16' (5 m), thereby allowing the device to be placed well away from the host computer 28. This, coupled with the devices very small size, substantially reduces the equipment anxiety that manifests itself in some patients, thereby easing the process of recording EVG. Although USB is the preferred embodiment because of its ubiquitous availability in standard personal computers, other serial (e.g., FireWire), optical or wireless (e.g, 802.11b) data communication systems may be used. Optical isolation 36 is necessary for any hardwired (e.g., cable connected) communication system for patient electrical isolation; the wireless system enhances patient isolation but at considerable additional cost and complexity.

The SPM 16 has on-board calibration specifically suited to EVG. The microcontroller 26 is able to switch in self-generated calibration signal(s) 27 into the amplifier 18 under control of the host computer software, which can then analyze the acquired waveform and determine if the system is performing within specification. The preferred and more traditional embodiment implements a single frequency sine wave, with a peak-to-peak voltage typical for the EVG (e.g., 200 micro volts peak-to-peak); the frequency is chosen to be in the middle of the passband of the filters. A second embodiment allows the host computer software to select specific single frequency waveforms that cover the center range of each of the diagnostic frequency bands (bradygastria or 1–2.5 cpm, normal or 2.5–3.75 cpm, tachygastria or 3.75–10.0 cpm, duodenal/respiratory or 10.0–15.0 cpm). A third embodiment implements one or more complex waveforms, consisting of two or more frequencies and selectable by the host computer software, with predetermined frequency content that could simulate an actual EVG. The latter is particularly unique and useful for ensuring that the SPM hardware amplifier gain, SPM hardware filter frequency response, SPM digital filter frequency response and diagnostic routines in the host computer software are also working correctly by simply selecting a simulated EVG waveform that simulates one or more of the diagnostic categories provided by the host computer software. Of course, the calibration waveforms can be adjusted for any electroviscerogram waveform.

Regarding waveform storage, the preferred embodiment has enough on-board memory 38 to hold the sampled and filtered data for a few minutes of data recording; the host computer software periodically acquires the data during the typical exam time of 45–60 minutes. The memory 38 can be part of or separate from the computer 28.

Figure 2:
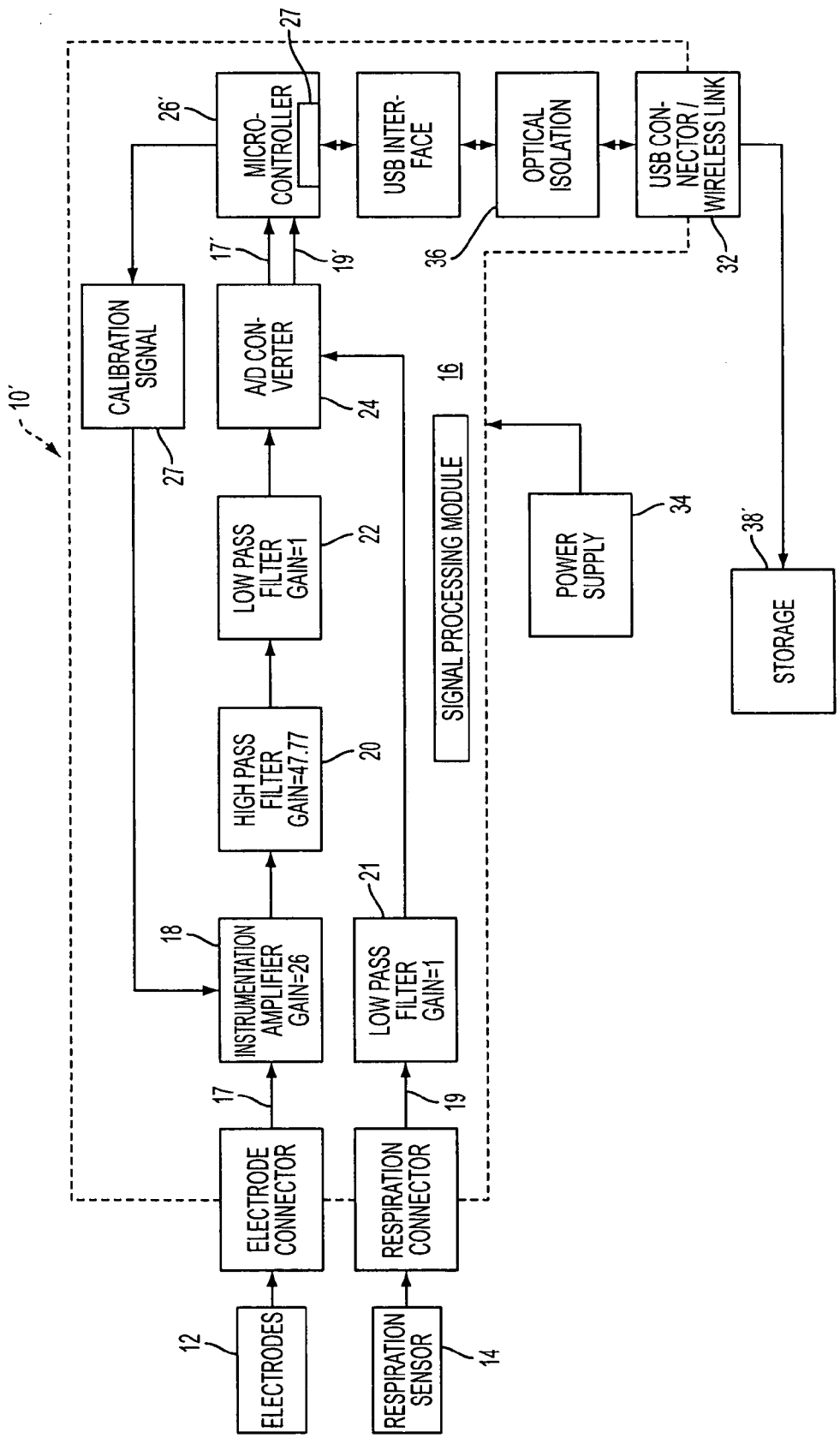
FIG. 2 is block diagram of an electroviscerogram system provided in accordance with a second embodiment of the invention.

With reference to FIG. 2, another embodiment of the system 10' is shown. In this embodiment, the micro-controller 26' includes a processor 27 that executes all the necessary software. Thus, the micro-controller 26' can be considered a processing device. Hence, the computer 28 of FIG. 1 need not be provided in the system 10'. The storage 38' provides enough on-board memory to store an entire exam's worth of data for later download. This type of storage is easily implemented on memory cards such as those used with digital cameras, thereby allowing the system 10' to be taken to any out-of-the-way clinic or home setting to conduct the patient exam, then download the data into a host computer back at a central office or hospital for analysis and diagnosis. Modern technology can also be implemented for transmitting the data in real time or immediately after the exam to a host system for more immediate diagnosis.

The system 10' can be entirely implemented as a stand-alone, highly portable system with the micro-controller 26' comprising one of the many hand held computers available even today, e.g., Palm OS or Windows CE based systems, and a plug-in SPM. These systems are small enough to be placed right next to the patient during data collection, and are capable of implementing the host computer functions including diagnostic assistance. Patient reports can be "printed" to a digital memory card (e.g., storage 38' of FIG. 2) for immediate insertion into a printer that accommodates these cards, causing the report to be printed as if it were a digital picture. Similar systems, regarding printing to digital memory card concept, are described in U.S. Pat. Nos. 5,827,179, 6,159,147 and 5,876,351, the contents of which are hereby incorporated herein by reference.

A method of and interpreting myoelectrical activity from an intra-abdominal organ includes using the electrodes 12 in order to obtain a plurality of first signals over time. These first signals are produced by a contractile, hollow internal organ of a living being. The signals include spurious signals as a result of artifact. The respiration sensor 14 obtains a second plurality of signals. These second signals are produced by the respiratory function of a living being, and include spurious signal indicative of artifact. The first and second signals are recorded simultaneously. The occurrence of artifact is identified by noting irregularities in both the first and second recorded signals during a specific time frame. Suitability of the non-artifactual signal is determined based upon uniformity of first and second signals during specific time comparison periods. A signal meeting criteria for suitability is subjected to computer analysis related to particular time periods. Computer calculation matches a suitable signal to established diagnostic patterns. The resultant device represents a novel apparatus with self-contained, auto-instructional, auto-controlling, and auto-interpretive methodology.

The following outlines define examples of software algorithms in accordance with the invention. The step can be implemented as executable code stored on a computer readable medium (e.g., a hard disk drive, a floppy drive, a random access memory, a read only memory, an EPROM, a compact disc, etc., executed by the computer 28 or micro-controller 26'.

EVG Artifact Identification

I. DEFINITION

A. EVG artifact identification is defined by voltage parameters of the recorded EVG signal. The program identifies these parameters.

B. The minutes during which the artifacts occur are marked and are not used for computer analysis of the EVG signal if agreed to by the operator.
C. The voltage parameters are the following:
   a. Zero (0) voltage signal with duration >5 sec
      i. Flatline
   b. High voltage signal
      i. Greater than 10 fold higher than the maximum voltage of the EVG signal as determined during the baseline recording
      ii. With duration greater than 5 sec
D. The baseline period is the standard upon which the post-water load EVG signal voltages will be assessed. At least four minutes of EVG with voltages >0 and <5000 micro volts must be obtained during the baseline recording period.
   a. These four minutes of EVG signal may be from any period of the baseline recording.
      i. For example, if the greatest signal amplitude during the baseline is 500 micro volts
         1. Then the upper limits of voltage allowed in the post water load period will be 5000 micro volts.
      ii. Baseline minutes may be selected by the program, but must be confirmed by the user.
      iii. User may override selected minutes and select 4–10 contiguous minutes if desired.
II. Protocol
A. Initially, Signal Test Mode is completed successfully, indicating that electrodes and respiration recording apparatus are functional.
   a. No flatline or offscale activity is present.
B. RUN feature is activated, and the 10-min baseline recording period begins.
C. The program assesses the EVG signal during the baseline period and prior to the water-loading phase for the following:
   1. An artifact free 4-minute segment of contiguous minutes
      a. This 4-minute period must be artifact free to set these parameters.
         i. 4 minutes up to a maximum of 10 minutes are permitted
      b. The operator must confirm that the baseline EVG minutes are artifact free since these minutes will be the standard upon which the post water load minutes of EVG will be assessed for artifact.
   2. The minimum and maximum voltage of the EVG signal during the selected 4-minute minimum of the baseline period is calculated.
D. Subsequently, the entire pre-water load, baseline, recording period of 10 min and the 30-min post-water load EVG signals will be subjected to the voltage parameters described under "Definition."
   1. For example, if the range of EVG amplitudes during the selected minimum of the 4 minute baseline recording is from 400 to 1200 micro volts
   a. Artifact is defined
      i. Flatline=zero (0) voltage for >5 sec
      ii. Offscale=voltage >12,000 micro volts for >5 sec.
E. The EVG signal recorded during the time indicated by the start and finish of the Water Load Phase are not evaluated for artifact since limb movement routinely creates artifact in the EVG signal.
F. The EVG recording continues for a period of 30 minutes from the completion of the Water Load Phase.
G. The three post-water load 10 minute periods of EVG recording are identified.
H. The three 10-min post-water load periods are identified and undergo the artifact identification protocol as detailed above.
   1. Each 10 minute segment is displayed in 4-minute segments.
      a. Minutes with artifact are identified separately and uniquely.
      b. Minutes without artifact are unmarked.
      c. Program will suggest to user a 4-minute minimum of artifact free, contiguous minutes.
         i. User selects or rejects minutes
            1. If suggested minutes are rejected, user is prompted to manually select minutes.
               a. Program verifies that selected minutes satisfy minimum conditions:
                  i. 4 minutes and continuous
   2. Similar operation occurs for
      a. The first 10 minutes post-water loading phase
      b. The second 10 minutes post-water loading phase
      c. The third 10 minutes post-water loading phase
   3. Splicing of minutes across 10-minute segments is not allowed.
   4. Splicing of non-contiguous minutes within 10-minute segments is not permitted.
   5. As most artifactual segments usually deform approximately 30 sec of EVG signal
      a. Acceptable minutes may initiate at the ½ minute mark
         i. This requires minutes to run ½ minute to the subsequent ½ minute in order to be used.
            1. i.e. Minute 1.0–2.0 vs. minute 1.5–2.5
   6. In a single 10-min period of EVG signal, splicing together of less than 4-minute contiguous recordings of EVG is not allowed.
      a. Additional and consecutive artifact-free minutes may be added to selected 4-minute segments in order to obtain the maximum number of minutes of EVG signal that can be analyzed.
      b. All selected minutes must be contiguous and not interrupted by artifact containing minutes.

Interpretation Module Protocols
I. Diagnostic/interpretive Categories
   a. Tachygastria
   b. Bradygastria
   c. Mixed Dysrhythmia
   d. Duodenal Arrhythmia
   e. Obstructive Gastropathy
   f. Normal
II. Diagnostic Parameters
   a. Program will interpret EVG post-water load test period
      i. Post-water load
   b. Appendices detail logic decision tree for each diagnostic category
III. User Considerations
   a. User will enter into the diagnostic module from the main menu bar
   b. Options will include
      i. View diagnostic module auto-interpretation
         1. Selection of diagnostic aid will present suggested interpretations to the user
         2. User will be prompted to
            a. Accept
               i. User accepts post-water load diagnoses b. Modify
  i. User selects post-water load to modify
  ii. User modifies diagnosis
    1. User prompted to accept changes
c. Reject
  i. If selected, user taken to manual interpretation mode
ii. Manual Interpretation
  1. Selection of manual interpretation will prompt user for:
    a. Post-water load diagnosis Minute Selection Protocol
I. Basic Parameters
a. Computer to select as a minimum, a "4-minute" continuous (consecutive minutes) segment
  i. Minutes are selected from four possible "10" minute segments
    1. 10 minute segments are as follows:
      a. Pre-water load
        i. Minutes 0–10 (Baseline)
      b. Post-water load
        i. Minutes 0–10 (10 minute post-water load)
        ii. Minutes 10–20 (20 minute post-water load)
        iii. Minutes 20–30 (30 minute post-water load)
  ii. If more than 4 minutes meet 'acceptable' criteria in a segment
    1. 4–10 continuous minutes may be selected
    2. Minimum of 4 continuous minutes must be 'selectable' to allow for recommendation of "ideal minutes."
      a. a "4-minute" segment need not start on a minute boundary but will start anytime the signal meets the acceptable criteria.
II. Selection Criteria
a. Acceptable minutes definition
  i. Minutes, which are not determined to be artifact.
    1. Must fall inside of the predetermined range.
      a. Different ranges are established for
        i. Pre-water load period
        ii. Post-water load period
b. Program will mark artifact minutes
  i. All unmarked minutes are acceptable minutes.
  ii. Program will select minutes from the pool of 'acceptable' minutes
  iii. Minimum associated criteria
    1. Within individual established 10 minute segment
    2. Selected minutes must be continuous/contiguous
    3. 4 minute minimum must be met
III. Reporting Criteria and Protocol
a. User interface
  i. Users will select Analyze Study from menu.
  ii. After analysis is noted to be complete
    1. Users will be prompted to
      a. View Selected Minutes vs. Select Minutes Manually
  iii. If Select Minutes Manually is selected
    1. Computer does not present auto-selected minutes
    2. User is presented with choice of four 10-minute periods to review
      a. Baseline or pre-water load
      b. Post-water load
        i. 0–10, 10–20, 20–30 periods
    3. All minutes from specifically selected 10 minute period are placed on the screen for user viewing and selection
    4. User will select minutes for analysis
    5. Same operation is repeated for all 4 periods
      a. All 4 periods must be reviewed to continue
  iv. If View Selected Minutes is selected and the program has been able to select adequate acceptable minutes for each segment
    1. User is presented with choice of which 10-minute segment to review
      a. Initially the 10 minute pre-water load or baseline period is presented
      b. Subsequently, the three post-water load periods are presented
    2. All minutes from specifically selected 10-minute period are placed on the screen for user viewing and selection
    3. Recommended minutes are marked with distinguishing overlay
    4. User is prompted to either
      a. Accept
        i. User prompted to select next period for viewing
        ii. If all periods have been completed user prompted to finish and/or enter interpretation mode
      b. Modify
        i. User is prompted to add to or subtract from suggested minutes
          1. After modification by user
            a. User will indicate or select "finished" by button click.
            b. Program re-evaluates to insure minimum of 4 continuous minutes selected
              i. "Minutes Accepted" if criteria met
              ii. If 4 minute criteria not met, user prompted to correct
        2. User prompted to select next period for viewing
        3. If all periods have been completed user prompted to finish and/or enter interpretation mode
      c. Reject
        i. User prompted to select minutes manually
        ii. User prompted to select next period for viewing
        iii. If all periods have been completed user prompted to finish and/or enter interpretation mode
  v. If computer is unable to select minutes based upon acceptable criteria for any/all periods.
    1. User is prompted to select minutes manually Test Mode Application
1. Definition
  a. Prior to being able to run an EVG study, test mode application will run
    i. Two components in test mode application
      1. Testing of signal integrity
        a. Combined signal from 3 patient electrodes
        b. Respiratory belt lead
        c. Eliminates "flat-line" or "off-scale" problems
        d. Insures proper electrode contact and function 2. Full patient signal evaluation
  a. To establish pre-baseline range parameters
    i. Specific to patient and study
    ii. Becomes range of normal against which baseline artifact is determined
  b. Eliminates baseline variance II. Testing of Signal Integrity Phase
 a. Specified components above will be evaluated for signal presence
    i. Time required—5–10 seconds
 b. If signal present w/adequate voltage
    i. Green light on screen graphic seen for each individual sensor
    ii. Test mode advances to patient signal evaluation
    iii. Adequate signal defined as
      1. >0–<5000 micro volts
 c. If signal not detected
    i. Red light on screen seen for specific sensor
    ii. Test mode holds until problem is corrected and retested
    iii. Signal not detected is defined as
      1. 0 voltage or flatline for period >1 second
 d. If signal too high
    i. Red light on screen seen for specific sensor
    ii. Test mode holds until problem is corrected and retested
    iii. Signal too high is defined as
      1. >5000 micro volts for >5 seconds=offscale III. Patient Signal Pre-Baseline Normal Range Evaluation Phase
 a. 30 seconds of patient tracing obtained from combined signal from the 3 abdominal electrodes
    i. Allows signal to stabilize w/o variance
 b. Range of stable signal voltage is determined
    i. This voltage range will be used to determine artifact in baseline or pre-water load portion of EVG
      1. If off-scale or flatline activity exists within the time allotted to establish normal base range
        a. Establishment of baseline normal range is shifted into the actual 10 minute baseline period or pre-water load testing
      2. If signal is stable, during this period, it may used to set the normal range by which to measure artifact in the baseline or pre-water load period
    ii. A multiple of this range will be used to determine artifact in the post-water load portion of EVG
      1. Multiple of 10 × baseline range
 c. Successful completion allows EVG to progress to run phase
    i. User will be prompted and allowed to begin study Diagnostic logic (e.g., the condition of a patient) can be obtained via software with reference to Tables 1–3.

TABLE 1

Post-Water Load Tachygastria Logic

| | Tachygastria Above Normal Range | Bradygastria Above Normal Range | 3CPM below Normal | Diagnostic Description |
|---|---|---|---|---|
| Post-water load | 3 | 0 | 3 | Tachygastria |
| | 3 | 0 | 2 | Tachygastria |
| Number of points present | 3 | 0 | 1 | Probable Tachygastria |
| | 3 | 0 | 0 | Probable Tachygastria |
| Post-water load | 2 | 0 | 3 | Tachygastria |
| | 2 | 0 | 2 | Tachygastria |
| Number of points present | 2 | 0 | 1 | Probable Tachygastria |
| | 2 | 0 | 0 | Probable Tachygastria |
| Post-water load | 1 | 0 | 3 | Probable Tachygastria |
| | 1 | 0 | 2 | Probable Tachygastria |
| Number of points present | 1 | 0 | 1 | Possible Tachygastria Clinical Correlation Required |
| | 1 | 0 | 0 | Possible Tachygastria Clinical Correlation Required |

If Tachygastria is noted . . . need to verify that respiratory rate is >8–14.

TABLE 2

Post-Water Load Bradygastria Logic

| | Tachygastria Above Normal Range | Bradygastria Above Normal Range | 3CPM below Normal | Diagnostic Description |
|---|---|---|---|---|
| Post-water load | 0 | 3 | 3 | Bradygastria |
| | 0 | 3 | 2 | Bradygastria |
| Number of points present | 0 | 3 | 1 | Probable Bradygastria |
| | 0 | 3 | 0 | Probable Bradygastria |
| Post-water load | 0 | 2 | 3 | Bradygastria |
| | 0 | 2 | 2 | Bradygastria |
| Number of points present | 0 | 2 | 1 | Possible Bradygastria Clinical Correlation Required |
| | 0 | 2 | 0 | Possible Bradygastria Clinical Correlation Required |
| Post-water load | 0 | 1 | 3 | Possible Bradygastria Clinical Correlation Required |
| Number of points present | 0 | 1 | 2 | Possible Bradygastria Clinical Correlation Required |
| | 0 | 1 | 1 | Probable Normal |
| | 0 | 1 | 0 | Probable Normal |

TABLE 3

Post-Water Load Duodenal Activity Logic

| | Tachygastria Above Normal Range | Bradygastria Above Normal Range | 3CPM below Normal | Duodenal/Respiratory Above Normal | Measured Respiratory Rate | Diagnostic Description |
|---|---|---|---|---|---|---|
| Post-water load Number of points present | NA | NA | NA | 3 | > or =15 | Duodenal Pacesetter Hyperactivity |
| | NA | NA | NA | 2 | > or =15 | Duodenal Pacesetter Hyperactivity |
| | NA | NA | NA | 3 | <15 | Respiratory Effect |
| | NA | NA | NA | 2 | <15 | Respiratory Effect |
| | NA | NA | NA | 1 | NA | NA |

Figure 3:
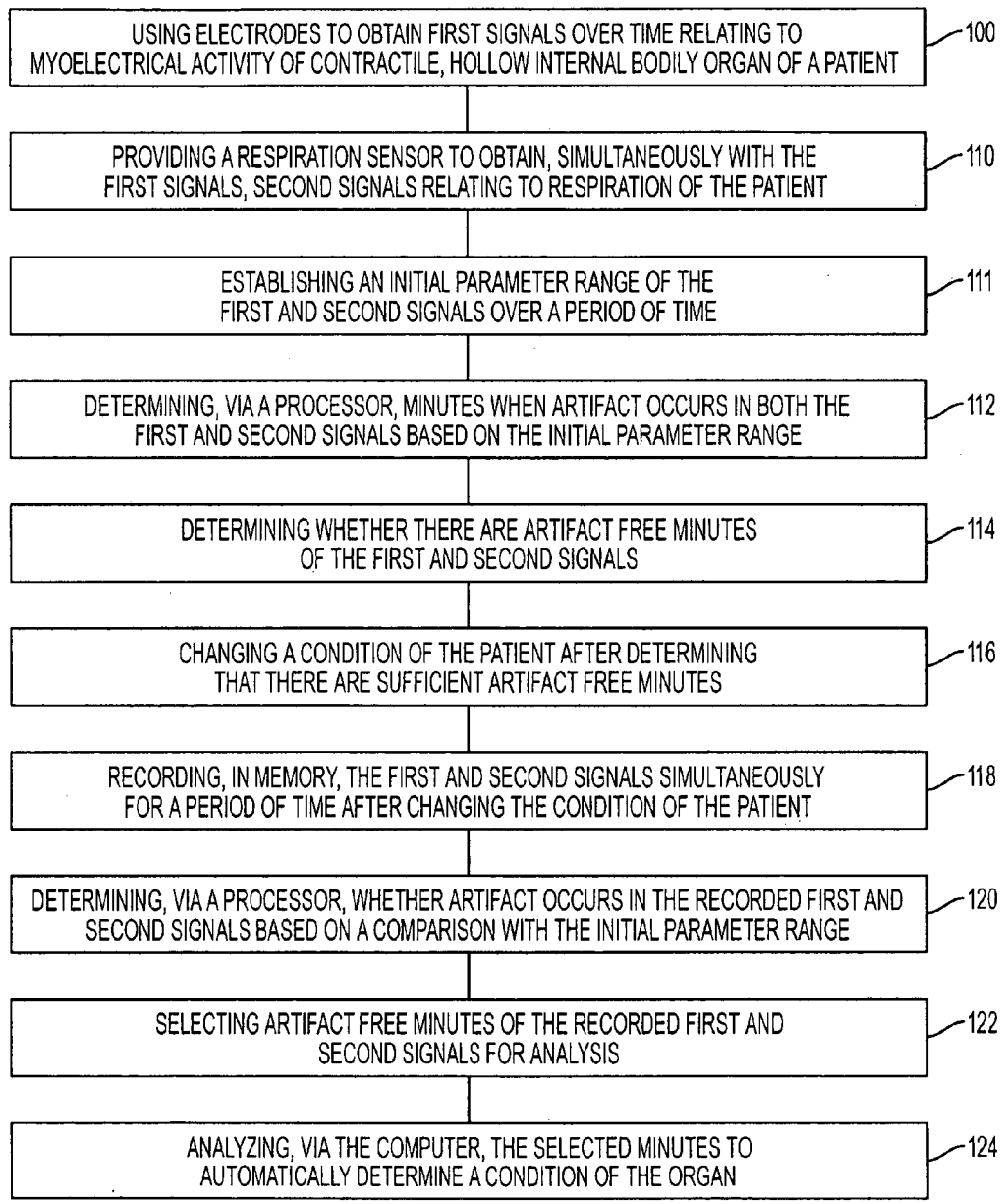
FIG. 3 is a flow chart of an embodiment of the invention.

Thus, by employing the algorithms outlined above, with reference to FIG. 3, a method of detecting and interpreting myoelectrical activity from an intra-abdominal organ includes, in step 100, using the electrodes 12 to obtain first signals over time relating to myoelectrical activity of the intra-abdominal organ of a patient. In step 110, the respiration sensor 14 is provided to obtain, simultaneously with the first signals, second signals relating to respiration of the patient. Next, a test mode can be performed to determine that the hardware and software interface that collects and interprets the signals is functioning properly and warns the user of the specific, if any, malfunction, and requires correction prior to continuation. This feature prevents studies from being conducted despite malfunction of the equipment, and directs the user as to the malfunction and corrective action needed to continue. In earlier systems, studies could continue despite the malfunction with the result being unrecognized invalid data and results, not to mention a waste of the patient and physician's time. For instance, if an electrode, electrode wire, respiratory sensor was malfunctioning, it would be reported and correction required prior to allowing the study to begin. Likewise the system acts proactively to signal the user that the functioning of system components is acceptable and that the study may proceed. Similarly, if during the performance of the study, a malfunction is noted in any hardware or software component, the user is notified and corrective action is then recommended, such as in the case of low battery power or disconnection of a lead or electrode.

After ensuring that the system is working properly, in step 111, an initial parameter range of the first and second signals is established over a period of time. Minutes (time) when artifact occurs in both the first and second signals are determined by the software in the host computer 28 in step 112, based on the initial parameter range of the first and second signals. In step 114, it is determined via a computer or processing device whether there are artifact free minutes of the first and second signals. It is preferred that these artifact free minutes be consecutive. If no artifact free minutes are determined, the test can be terminated at this point.

In step 116, a condition of the patient is changed after determining that there are sufficient artifact free minutes. When testing the stomach, this step can include performing the water load test. When testing the bladder, this step could include the water load test or a drug challenge and when testing the intestine/colon, step 116 can include a food or water load or a drug challenge.

The first and second signals are recorded in memory simultaneously in step 118 for a period of time after changing the condition of the patient in step 116. In step 120, it is determined, via software, whether artifact occurs in the recorded first and second signals based on a comparison with the initial parameter range. Next, in step 122, artifact free minutes (preferably consecutive minutes) of the recorded first and second signals are selected for analysis. The artifact free minutes are selected automatically via software, but a user may override selected minutes. In step 124, via the computer 28 (FIG. 1) or micro-controller 26' (FIG. 2), the selected minutes are analyzed to automatically determine a condition of the organ. For example, the analyzing step may include automatically (not manually) determining a condition of the organ to be one of tachygastria, bradygastria, mixed dysrhythmia, duodenal arrhythmia, obstructive gastropathy and normal.

The system and method of the embodiment are not limited to the stomach, but are applicable to any contractile hollow organ. For example, if the bladder is tested, the system could automatically determine the condition of the bladder to be one of the following:
Obstructive Uropathy
Bladder Atony
Hypermotility/Hyperactive Uropathy
Hypomotility/Hypoactive Uropathy
Bladder Spasm/Spastic Uropathy
Mixed/Non-specific Uropathy
Retrograde Uropathy If intestine/colon is tested, the system could automatically determine the condition of the intestine/colon to be one of the following:
Obstruction
Hypermotility/Hyperactive Dysmotility
Hypomotility/Hypoactive Dysmotility
Spasm/Spastic Dysmotiltiy
Mixed/Non-specific Dysmotility
Retrograde Motility/Dysrythmia In testing the intestine/colon, multiple sets of electrodes can be employed with multiple signals 17' being received by the processing device, e.g., micro-controller 26' or computer 28.

The Intelligent, auto-controlling process described above provides real-time instruction and auto-analyze incoming signals to determine signal and process adequacy. Simultaneous with the real-time use of the system, technical guidance is provided to the operator performing the study to correct problems recognized by the system. After completion of the study, intelligent, internal, auto-interpretive processes select signals for interpretation, analyze results, and provide printed analyses and suggested diagnoses, as an integral part of the process of signal acquisition, processing, and analysis.

Features of the invention include:
1. Ability to connect to existent user networks
   a. Allows results to be printed using network resources such as shared color laser printers.
   b. Allows remote access to patient files and results from within local area network.
2. Ability to connect to Company website.
   a. Allows uploading of files for review or advise.
   b. Allows upgrading of software from manufacturer.
   c. Permits multi-site research initiatives with confidential HIPPA compliant uploading of data and diagnosis.
   d. Permits technical troubleshooting on the local platform from a distance.
3. Single component unit with adjustable, connected touch screen flat panel monitor.
   a. Built in to the unit will be all needed components.
   b. Options include:
      i. Modem
      ii. Network Card
   c. B/W platform bed printing included
   d. Touch screen based interface
   e. Mouse and keyboard connection ports
4. In addition to the international standardization protocol, there is a research protocol arm to allow totally open architecture in the EVG/EVG study with the same auto correction, auto interpretation, and auto diagnostics.
5. There is a built in capability for dial-in and/or web based remote diagnostics for troubleshooting purposes of the device.
6. The system will also be capable of generating billing information and printing/transmitting this info.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of detecting and interpreting myoelectrical activity from a contractile, hollow internal bodily organ, the method including:
   using electrodes to obtain first signals over time relating to myoelectrical activity of contractile, hollow internal bodily organ of a patient,
   providing a respiration sensor to obtain, simultaneously with the first signals, second signals relating to respiration of the patient,
   establishing an initial voltage range of the first and second signals for a specific amount of time thereby defining a normal operating voltage range specific to a patient under study,
   determining, via a processor, minutes when artifact occurs in both the first and second signals based on the normal operating voltage range,
   determining, via the processor and absent manual interpretation, whether there are artifact free minutes of the first and second signals,
   changing a condition of the patient after determining that there are sufficient artifact free minutes,
   recording, in memory, the first and second signals simultaneously for a period of time after changing the condition of the patient,
   determining, via the processor and absent manual interpretation, whether artifact occurs in the recorded first and second signals based on a comparison with the normal operating voltage range,
   selecting, via the processor and absent manual interpretation, artifact free minutes of the recorded first and second signals for analysis, and
   analyzing, via the processor and absent manual interpretation, the selected minutes to automatically determine a diagnosis of the condition of the organ.

2. The method of claim 1, wherein the step of changing a condition of the patient includes establishing a water load in the stomach of the patient.

3. The method of claim 2, wherein the organ is the stomach and the step of analyzing includes determining a diagnosis of the condition of the organ to be one of tachygastria, bradygastria, mixed dysrhythmia, duodenal arrhythmia, obstructive gastropathy and normal.

4. The method of claim 1, wherein the determining step includes ensuring that the processor can determine automatically a diagnosis of condition of the stomach, bladder and intestine, respectively.

5. The method of claim 1, wherein the first signals are filtered prior to the step of determining minutes when artifact occurs.

6. The method of claim 5, wherein the first signals are converted from analog signals to digital signals, the filtering includes using at least one analog filter with a certain cut-off frequency range to filter the analog signal and using a digital filter, with a cut-off frequency range that is narrower than the certain cut-off frequency range, to filter the digital signals.

7. The method of claim 6, wherein the digital filter is provided on a computer readable medium.

8. The method of claim 1, wherein the first signals are amplified by an amplifier, and a controller that includes the processor is associated with the amplifier, the method further includes a calibration step wherein the controller sends a calibration signal to the amplifier with the processor analyzing a waveform based on the calibration signal, the calibration signal being in a diagnostic frequency range of the contractile, hollow internal bodily organ.

9. The method of claim 8, wherein the calibration signal is a sine wave of a certain frequency within a pass band of a filter that filters the first signal.

10. The method of claim 8, wherein the diagnostic frequency range is a frequency range that that defines one of tachygastria, bradygastria, mixed dysrhythmia, duodenal arrhythmia, obstructive gastropathy and normal condition of the stomach.

11. The method of claim 8, wherein the calibration signal simulates a first signal.

12. The method of claim 1, wherein the step of determining minutes when artifact occurs includes monitoring a ten-minute period of time.

13. The method of claim 1, wherein the step of selecting artifact free minutes includes selecting consecutive artifact free minutes.

14. The method of claim 1, wherein the memory is a storage device associated with the processing device and the method further includes storing obtained data associated with the organ in the storage device.

15. The method of claim 1, wherein prior to the establishing step and during the subsequent steps, the method further includes determining whether a malfunction exists and if a malfunction exists, warning a user of the malfunction so that the user can correct the malfunction and continue with the method.

16. A system for detecting and interpreting myoelectrical activity from a contractile, hollow bodily organ, the system comprising:

electrodes constructed and arranged to obtain first analog signals over time relating to myoelectrical activity of a contractile, hollow bodily organ of a patient, a respiration sensor constructed and arranged to obtain, simultaneously with the first signals, second analog signals relating to respiration of the patient, filtering structure constructed and arranged to filter the first and second analog signals, an analog to digital converter constructed and arranged to convert the filtered first and second analog signals to respective first and second digital signals, a processing device constructed and arranged to receive the first and second digital signals, the processing device being configured for executing instructions for 1) establishing an initial voltage range of the first and second digital signals for a specific amount of time thereby defining a normal operating voltage range specific to a patient under study, 2) determining whether artifact occurs in the first and second digital signals based on an analysis of the first and second digital signals and the normal operating voltage range and absent manual interpretation, and 3) analyzing artifact free minutes of the first and second digital signals thereby determining automatically, and absent manual interpretation, a diagnosis of the condition of the organ, and a storage device associated with the processing device constructed and arranged to store data received from the processing device.

17. The system of claim 16, wherein the organ is the stomach and the sequence of instructions includes instructions for determining a condition of the organ to be one of tachygastria, bradygastria, mixed dysrhythmia, duodenal arrhythmia, obstructive gastropathy, and normal.

18. The system of claim 16, wherein the filtering structure includes analog filter structure constructed and arranged to filter the analog signals that are within a certain frequency range, the system further comprising a digital filter constructed and arranged to filter the digital signals that are within a frequency range that is narrower than the certain frequency range.

19. The system of claim 18, wherein the analog filter structure includes a high pass analog filter and a low pass analog filter.

20. The system of claim 16, further comprising an amplifier constructed and arranged to amplify the first analog signals and a controller that includes the processor associated with the amplifier such that the controller provides a calibration control signal to the amplifier, the processing device including a processor constructed and arranged to analyze a waveform based on the calibration signal, the calibration signal being in a diagnostic frequency range of the contractile, hollow internal bodily organ.

21. The system of claim 20, wherein the filter structure, the analog to digital converter and the processing device are part of a module, the module communicating with the storage device via one of a universal serial bus (USB) connection and a wireless signal transmitter.

22. The system of claim 16, wherein the storage device is a digital memory card.

23. The system of claim 16, further comprising a battery to power components of the system.

24. The system of claim 16, wherein the processing device is a portable, hand-held device.

25. The system of claim 16, wherein the processing device is a host computer.

26. A system for detecting and interpreting myoelectrical activity from a contractile, hollow bodily organ, the system comprising:

means for obtaining first analog signals over time relating to myoelectrical activity of a contractile, hollow bodily organ of a patient, means for obtaining, simultaneously with the first signals, second analog signals relating to respiration of the patient, means for filtering filter the first and second analog signals, means for converting the filtered first and second analog signals to respective first and second digital signals, processing means for receiving the first and second digital signals, establishing an initial voltage range of the first and second digital signals for a specific amount of time thereby defining a normal operating voltage range specific to a patient under study, determining whether artifact occurs in the first and second digital signals based on an analysis of the first and second digital signals and the normal operating voltage range and absent manual interpretation, and for analyzing artifact free minutes of the first and second signals thereby determining automatically, and absent manual interpretation a diagnosis of the condition of the organ, and means for storing data received from the processing means.

27. The system of claim 26, wherein the processing means is a portable, hand-held processing device, and the means for storing is a digital memory card separate from the processing device.

28. The system of claim 26, further comprising means for amplifying the first analog signals, and wherein the processing means is associated with the means for amplifying to provide a calibration control signal to the means for amplifying, the processing means including a processor constructed and arranged to analyze a waveform based on the calibration control signal, the calibration control signal being in a diagnostic frequency range of the contractile, hollow internal bodily organ.

* * * * *